United States Patent [19]
Wilkes et al.

[11] Patent Number: 5,816,403
[45] Date of Patent: Oct. 6, 1998

[54] STERILIZABLE CONTAINER FOR STERILE PRESENTATION OF CONTENTS

[76] Inventors: Kenneth R. Wilkes, 55 Brookwood Rd.; Lyman R. Marshall, 110 Robin Hood Rd., both of Asheville, N.C. 28804

[21] Appl. No.: 923,286

[22] Filed: Sep. 4, 1997

[51] Int. Cl.⁶ .................................................... B65D 85/00
[52] U.S. Cl. ............................................................ 206/438
[58] Field of Search ................................... 206/363, 370, 206/438, 439, 440; 220/87.1

[56] References Cited

U.S. PATENT DOCUMENTS

| | | | |
|---|---|---|---|
| 4,352,429 | 10/1982 | Newman | 206/439 |
| 5,257,692 | 11/1993 | Hecox | 206/438 X |
| 5,669,909 | 9/1997 | Foster | 206/438 X |

*Primary Examiner*—Jacob K. Ackun
*Attorney, Agent, or Firm*—Saul Epstein

[57] ABSTRACT

A sterilizable container which includes an internal flap or a chute which is deployed when the container is opened to provide a sterile passageway through which the stored items may be removed. The flap or chute shields the contents of the container from contact with unsterile areas while the removal is in progress.

18 Claims, 6 Drawing Sheets

STERILIZABLE CONTAINER FOR STERILE PRESENTATION OF CONTENTS

BACKGROUND OF THE INVENTION

One of the very important matters which concerns surgical practitioners is the maintenance of sterility in operating rooms. As a result, many products and procedures have been developed to assure the sterility of items to be used in surgery, both during their storage and to achieve an aseptic presentation to the surgeon and other members of the operating team. Surgical items are normally stored in an unsterile environment, i.e., in ordinary storage rooms. Nevertheless, these items must be presented at time of use to members of the operating team in a sterile condition. Prior to the present invention, containers of many types were available for sterile storage in an unsterile environment, but for many products used in the course of surgery, aseptic presentation was awkward, and the packaging required to assure aseptic presentation was relatively expensive.

For example, surgical gowns are commonly wrapped in a non-woven cloth-like material called "CSR Wrap" (which is an abbreviation of "Central Supply Room Wrap") and then sealed in a plastic pouch for long term storage. The procedure for wrapping the gown in CSR Wrap is very detailed so that the gown can be uncovered at a later time and presented to the ultimate user without compromising sterility. After packaging, the gown is sterilized by either radiation (ionizing radiation) or gas (ethylene oxide (ETC) or steam (autoclaving)). Proper package design permits storage for extended periods in a non-sterile environment. In the operating room, the package is opened by a non-sterile nurse, and the CSR Wrapped gown placed on a table. While the exterior of the CSR Wrap is unsterile (because of handling by the non-sterile nurse), the interior is still sterile, as are the contents. The nurse then carefully unfolds the CSR Wrap, using care not to touch the gown or the interior of the wrap. At this point the gown is laying exposed on a sterile field (the inside of the CSR Wrap). A surgeon can then pick up the gown and put it on by slipping his or her arms into the sleeves (which are easily accessible because of the way in which the gown is folded).

The means of storage and presentation of items to operating room personnel, as described above, is both awkward and expensive, and there is a need for improvement.

A great many constructions for containing sterile items have been devised over the years. Examples of such constructions may be found illustrated in U.S. Pat. Nos. 3,754,700, 4,367,816, 5,549388, and 5,551,781. All of these pouch designs are capable of being fabricated so as to maintain sterility of the contents. However, since the access opening in all of the foregoing designs is surrounded by non-sterile regions, there is great danger, even with care, that the stored item might touch a non-sterile area when being removed. Consequently, these prior art packages (without internal wrapping) have not seen use in operating room environments in connection with items such as surgical gowns.

Consequently, it is an object of the present invention to provide packaging for items to be used in an operating room environment or the like which is less expensive than that presently used.

It is another object of the present invention to provide packaging for items to be used in an operating room environment or the like which permits aseptic presentation of the items to operating room personnel without the necessity of using CSR Wrap or other inner wrapping.

Other objects and advantages of the present invention will become clear to persons skilled in the art from a reading of the following specification taken with reference to the appended drawings.

SUMMARY OF THE INVENTION

Conventional packaging for sterile items takes many forms. One such form, for example, is known as a "header" bag or pouch. Header bags are so named because they utilize a peelable cover over the access opening at one end (the head) of the bag. A header bag, in its common form, includes two flat flexible plastic sheets having the same width, but one shorter than the other. At the time of manufacture, the sheets are seamed together along the two sides (normally using heat and pressure) with one end (with the edges aligned) left open and the other end (with one sheet extending beyond the other) covered with a "tear strip". A tear strip is a sheet of material that covers the access opening of a package and is at least partially peelably attached to the package. Access to the contents of the package is gained by peeling open the peelable seams of the tear strip to uncover the access opening. The tear strip is usually completely removed from the package when access is desired.

Subsequent to manufacture of the pouch, the item or items to be stored are inserted through the open end of the pouch, and the open end then sealed closed, using heat and pressure or adhesives as desired. If the pouch is intended for gas sterilization, the tear strip is ordinarily made of a material which is porous with respect to the sterilizing gas (e.g., ethylene oxide (ETO) or steam), but impervious to bacteria and the like. It is known by those skilled in the art that while header bags intended for gas sterilization require some porous region, and that region is usually on the tear strip, the tear strip could be impervious to gas and the required porous region could be elsewhere. Pouches intended for radiation sterilization need not have a gas permeable region.

Header bags are capable of maintaining sterility of the contents for extended periods of time after sterilization. When it is desired to use the stored item(s), the tear strip is peeled from the package, and the contents removed. Unfortunately, the edges of the pouch around the tear strip (i.e., around the access opening), having been exposed during storage, are not necessarily sterile, and contact with these edges by the stored item(s) upon removal, is likely to compromise sterility. Accordingly, as previously mentioned, it has been customary to use an internal wrapping around the sterile items, such as CSR Wrap, so as to avoid contact between the unsterile edges of the bag and the sterile item(s).

Containers according to the present invention do not require an inner wrapping in order to preserve sterility of the contents when being presented to operating room personnel. The invented container construction is such that the danger of contacting unsterile areas of the container when the contents are removed is extremely low. In the invented package, the contents of the package are protected from contact with unsterile areas by a flap or a "chute" which is wholly contained within the package and which is deployed upon opening the package to shield the contents from any unsterile areas of the package near the path of egress. Contact with unsterile areas as the stored item(s) are removed, is thus avoided.

DETAILED DESCRIPTIONS OF THE INVENTION

The storage volume portion of the invention in the embodiments described herein may be fabricated from flexible plastic sheets, e.g., low density polyethylene, which are seamed to each other so as to form the storage volume, however some portions of the packages can be semi-rigid or rigid (e.g., trays), if desired. Materials other than plastic may also be used, as will be appreciated by those skilled in the art. In the following description, the invention is described in connection with (variously) "packages", "containers", "pouches", and "bags". While these terms involve different degrees of generality, it should be understood that the invention is applicable to any and all of the foregoing, even though a particular embodiment may be described in connection with one of the more specific terms.

Biologic seams, i.e., seams which are intended be impervious to biological organisms, are shown on the drawings as heavy solid lines. References to tack seams (which are indicated on the drawings by heavy dashed lines) are intended to convey that the indicated seams need not form a biological seal, but only that the affected sheets are attached. Tack seams could, for example, be formed from a series of disconnected dots, or be continuous seams, as is convenient. Both types of seams are ordinarily made by the application of heat and pressure for specified times, but in some cases adhesives will be found appropriate.

For purposes of clarity, the ends of some of the seams in the exploded views are shown connected by dotted lines. The dotted lines signify that the affected sheets are joined together at the seams indicated. Also for clarity, seam lines appearing on the various portions of the package which are part of a single seam are indicated by the same reference number.

Several of the embodiments described include some elements which are common to other embodiments. For clarity and ease of understanding, these elements are usually referred to using the same reference numbers. Finally, many different materials may be used to fabricate the various parts of the packages described herein, and references thereto should be taken as illustrative and not limiting. Examples of some of the materials useful in connection with the present invention are: low density polyethylene (with and without high slip additives and/or coatings to achieve peelability), surgical paper, metallic foil, and spun olefins.

Figure 1:
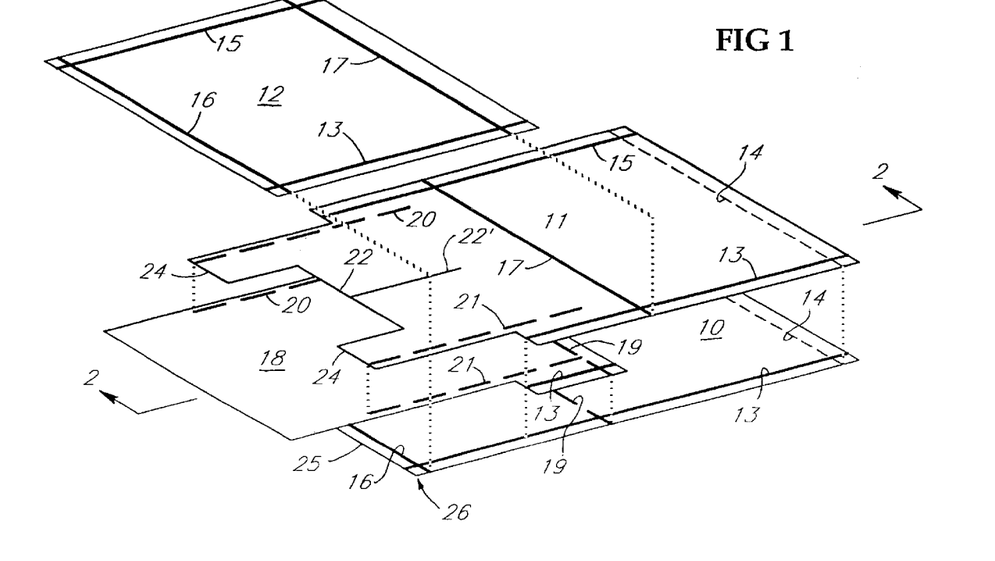
FIG. 1 is an exploded trimetric view of a first embodiment of the invented package. The package is shown in the open condition.

FIG. 1 shows a pouch which is known to the trade as a header bag. A header bag consists of a bottom wall 10, a top wall 11, and a tear strip 12 seamed together with seams 13, 14, 15, 16, and 17. Seam 14 (which is a biologic seam) is shown as light dashes because this seam is normally made after initial pouch fabrication has been completed, and the contents to be stored have been inserted.

The space between walls 10 and 11 (held together by seams 13, 14, and 15) form a volume in which the items to be stored are held. An access opening, i.e., the opening through which the contents are removed at time of use, is at the end of the pouch opposite seam 14, and is covered by tear strip 12. At the time the stored items are to be removed, tear strip 12 is torn off the package, and the exposed contents removed. The tear strip 12 is displaced sideways in the exploded views for clarity.

The seams which attach walls 10 and 11 are preferably of the "permanent" type, i.e., difficult or impossible to break. Ordinarily, with permanent type seams, the wall material will rupture before the seams separate. On the other hand, the seams which attach tear strip 12 to walls 10 and 11 are "peelable", i.e., they are seams made such that the tear strip can be peeled from the package without rupturing either the tear strip or the package wall. Peelable seals are generally of two types, one being where the seam itself is weak enough to rupture when the seam is peeled open, and the other being where one of the walls is comprised of two or more laminations, and one of the laminations delaminates from the wall during the peel process. Commonly, tear strip seams have a peel strength of about 1 lb per inch. Control of seam strength is obtained by a combination of material selection and the time/temperature/pressure conditions used to create the seam. Generally, the mating materials are chosen depending on whether a particular seam is to be peelable or permanent, and the time/temperature/pressure conditions are adjusted to attain the precise tear strength desired. For example, walls 10 and 11 could be made of low density polyethylene, which forms a permanent seam when seamed to itself, and the tear strip could be made of surgical paper or Tyvek (a spun olefin manufactured by the DuPont Company) which has been coated with a substance which makes a peelable bond to low density polyethylene.

Tear strips for header bags made for gas sterilization (ETO or steam) are commonly porous to the extent that they permit the flow of the sterilization gas in and out of the pouch, but they do not permit bacteria or the like to enter. A particularly suitable tear strip for gas sterilizable containers is described in U.S. Pat. No. 4,367,816. Tear strips made according to the principles enunciated in that patent combine good breathability and a non-shredding structure. Tear strips for bags intended for radiation sterilization need not be gas permeable, and are normally impervious. If the walls 10 and 11 are made of low density polyethylene, the tear strip for a radiation sterilizable pouch could be made of low density polyethylene with a coating of a blend of ethyl vinyl acetate and low density polyethylene, which mixture forms a peelable bond to low density polyethylene.

Header bags as described above are well known, and in common use. However, as mentioned, in the form known in the prior art, header bags are not suitable, for example, to store surgical gowns for operating room use unless an internal wrap (i.e., CSR wrap) is used. The following described modifications of the conventional header bag will make such a bag suitable for operating room use with items such as surgical gowns.

Figure 2:
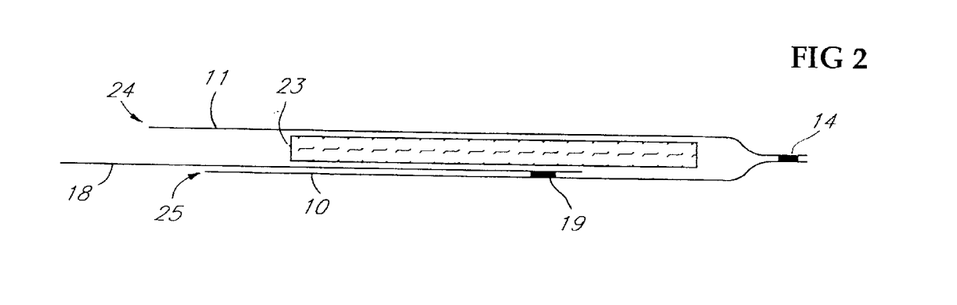
FIG. 2 is a cross sectional view of the package of FIG. 1, taken at 2—2 of FIG. 1.
Figure 3:
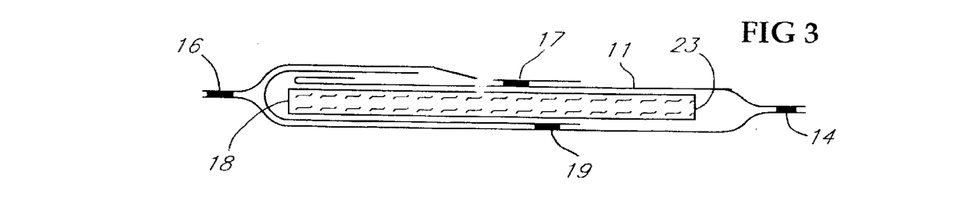
FIG. 3 is a cross sectional view of the first embodiment of the invention similar to FIG. 2 except that the package is shown closed.

Referring still to FIGS. 1–3, a flap 18 is shown tack seamed to bottom wall 10 along tack seam 19, and to top wall 11 along tack seams 20 and 21. Flap 18 is preferably made slightly narrower than the distance between seams 13 and 15 for a portion of its length so that its end can fold over top wall 11 within the seams. It can either be tapered somewhat or cut rectangularly, as shown in FIG. 1. The flap 18, when unfolded, as seen in FIGS. 1 and 2, lies over (and covers) the unsterile edge of bottom wall 10 outboard of seam 16, and so prevents the contents of the pouch (indicated by reference 23 in FIGS. 2 and 3) from contacting an unsterile area when being removed from the pouch. The flap 18 is preferably made of a material which will not take a crease, so that it will deploy without effort when the tear strip is removed. As shown in FIG. 3, flap 18 preferably overlaps wall 11 when the pouch is unopened, but the amount of overlap, if any, is a matter of preference for a particular application.

In the embodiment of the invention illustrated in FIGS. 1–3, edges 24 of wall 11 preferably extend beyond edge 25 of wall 10 when flap 18 is deployed. This construction provides a "chute" between wall 11 and flap 18 through which the pouch contents must pass when being withdrawn from the pouch, shielding the contents from contact with any unsterile portion of wall 10. Wall 11 preferably has a cut out section 22 to enable the receiver of the pouch contents to grasp the contents easily when offered. The size and shape of the cutout depends on the nature and size of the article(s) to be stored. A slit 22' could be used in addition to, or instead of cutout. 22, if desired, to facilitate removal of the contents.

If the edges 24 of wall 11 do not extend beyond edge 25 of wall 10 when flap 18 is deployed, there can be some danger that if the recipient of the contents is careless, the contents could brush against (for example) unsterile corner 26 of wall 10 while being removed. While the flap 18 itself provides significant protection as compared to prior art construction, it is preferred that more protection yet be provided, as by extending the edges 24 beyond edge 25.

Figure 4:
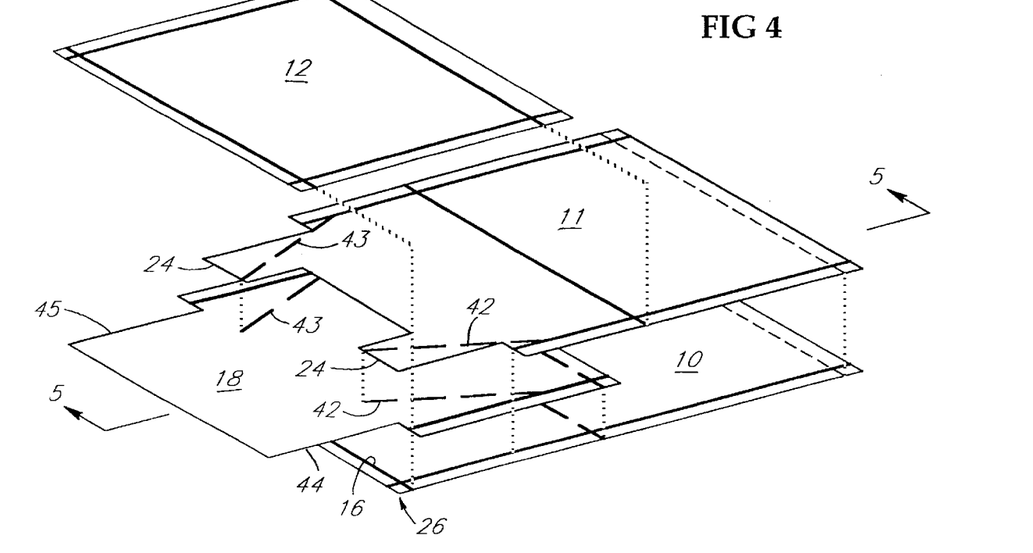
FIG. 4 is an exploded trimetric view of a variant of the invented package as shown in FIGS. 1–3. The package is shown in the open condition.
Figure 5:
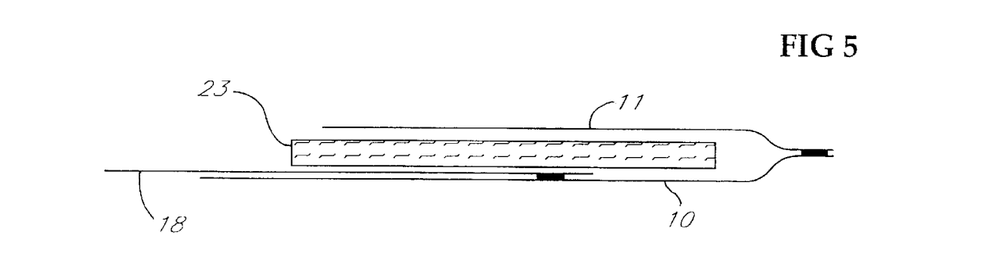
FIG. 5 is a cross sectional view of the package of FIG. 4, taken at 5—5 of FIG. 4.
Figure 6:
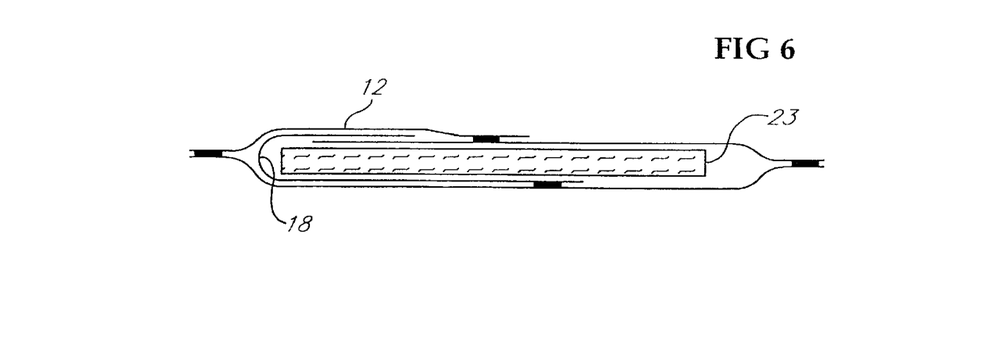
FIG. 6 is a cross sectional view of the second embodiment of the invention similar to FIG. 5 except that the package is shown closed.

FIGS. 4, 5, and 6 depict a variant of the embodiment illustrated in FIGS. 1, 2, and 3. This variant ameliorates the problem just described in the case where the wall 10 is made short of the end of the pouch. It is similar to that illustrated in FIGS. 1, 2, and 3, but the edges 24 are short of seam 16. In the embodiment of FIGS. 4, 5, and 6, the danger of contact between the contents of the pouch and corner 26 is reduced by providing a pair of seams 42 and 43 between wall 11 and flap 18 to form a tapered chute through which the contents of the container are removed. Seams 42 and 43 terminate some distance inboard of edges 44 and 45 of flap 18 so that the probability of inadvertent contact between the contents of the container and a possibly unsterile region is reduced.

Since certain areas of the containers described herein are sterile when the stored items are presented for use, and other areas are not necessarily sterile, it is preferable to color the sterile areas an appropriate color, for example blue, and the not necessarily sterile areas another color, for example white. Such color coding provides additional confidence to the ultimate user that sterility is not being compromised by the procedure being used. Color coding can be done by coloring the film itself, by using multilayered films with colored additives and/or by printing, as convenient.

If color coding is to be done, it will be noticed that in the embodiments described above, sheet 11 includes one area (the area adjacent to seam 14) which would be color coded white, and another area (the area which includes seams 21) which would be color coded blue. This two colored sheet could conveniently be created by printing either the white area on a blue sheet, or the blue area on a white sheet, but printing on areas which include seams can possibly suffer problems (e.g., smearing) at the seams, and hence it might be desired to avoid the necessity of printing such areas. A second embodiment of the invention, which permits color coding without the necessity of printing areas which include seams, is illustrated in FIGS. 7, 8, and 9.

In this embodiment, the chute which protects the contents of the pouch from contamination while being removed from the package is formed by flap 18 and sheet 70, both of which can be made of material which is blue without printing. These sheets are seamed together by tack seams 71 and 72. Tack seam 73 attaches the back of sheet 70 to wall 11. When deployed, as seen in FIG. 7, the edges 74 preferably extend beyond edge 25. It will be appreciated that instead of sheet 70 and flap 18 being two separate pieces, an equivalent structure could be realized by making these two elements parts of a flattened tube. In this case, the width of the flattened tube would be less than the distance between seams 13 and 15, and the sides of the tube would be held inside the container by tack seams 19 and 73. The term "chute", as used herein, is intended to describe a passageway for the contents of the package, whether seamed or seamless. That is to say that while this specification refers to seams at various places, those skilled in the art will understand that no actual seam between two physically separate sheets need exist, but rather the described "sheets" on either side of the "seam" can be parts of a single sheet.

Figure 7:
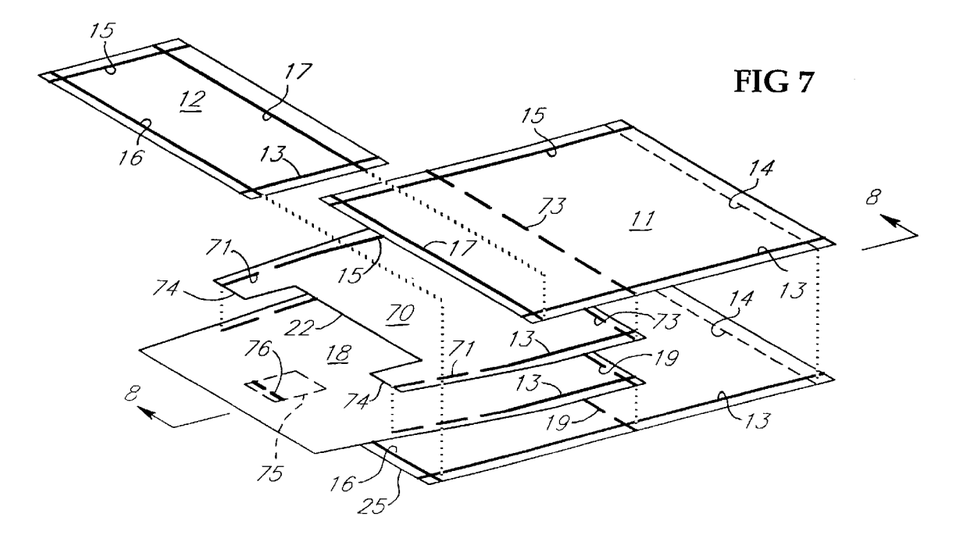
FIG. 7 is an exploded trimetric view of a second embodiment of the invented package. The package is shown in the open condition.
Figure 8:
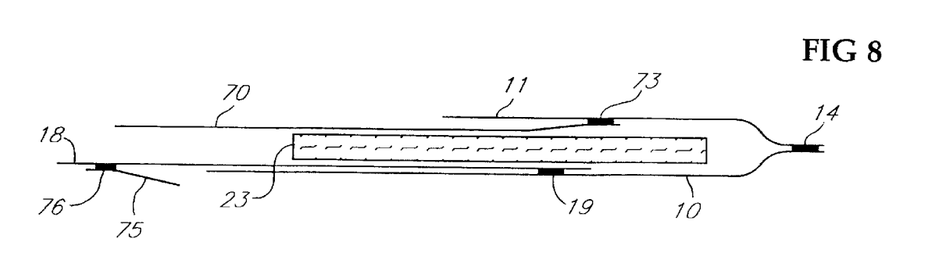
FIG. 8 is a cross sectional view of the package of FIG. 7, taken at 8—8 of FIG. 7.
Figure 9:
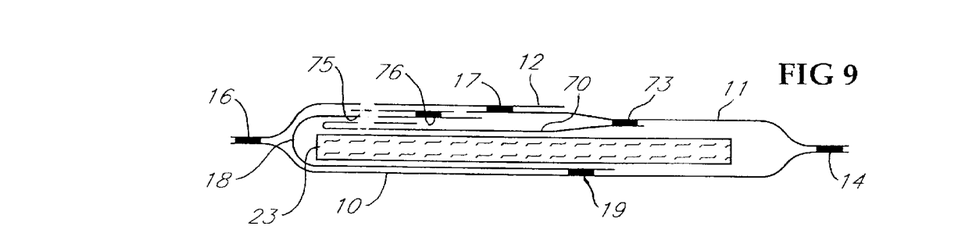
FIG. 9 is a cross sectional view of the second embodiment of the invention similar to FIG. 8 except that the package is shown closed.

An additional feature shown on the embodiment of FIGS. 7–9, but, as will be appreciated, is also applicable to other embodiments, is tab 75, which is attached to flap 18 by tack seam 76. Particularly if flap 18 is made long enough to tuck under wall 11 when the pouch is sealed (as is shown in FIG. 9), the chute may not deploy without assistance. In this case, tab 75 will allow the flap 18 to be pulled free by the opening nurse.

Figures 10, 11:
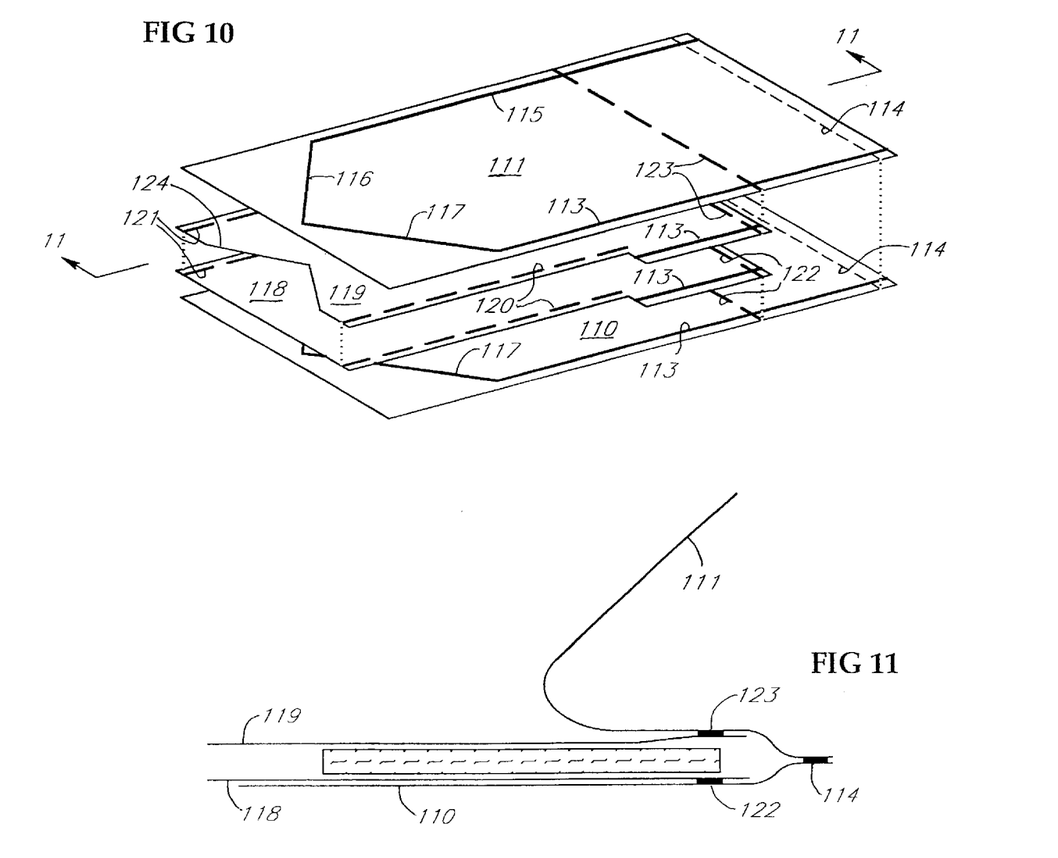
FIG. 10 is an exploded trimetric view of a third embodiment of the invented package.
FIG. 11 is a cross sectional view of the package of FIG. 10, taken at 11—11 of FIG. 10. The package is shown open.
Figure 12:
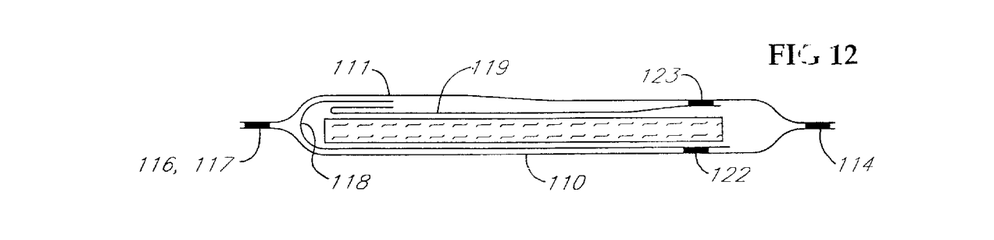
FIG. 12 is a cross sectional view of the third embodiment of the invention similar to FIG. 11 except that the package is shown closed.

FIGS. 10, 11, and 12 show still another embodiment of the invention. These figures show the invention as applied to a "chevron" type bag wherein the seal on one end has a "V" or "chevron" shape. A chevron type bag consists basically of two sheets (walls 110 and 111) seamed together at seams 113, 114, 115, 116, and 117. The aforementioned seams are ordinarily all peelable, and one of the walls, e.g., 111, is made permeable to the sterilizing gas in bags made for gas sterilization. As in the previous embodiments, seam 114 (shown in light dashed lines) is made after the pouch has been fabricated and the items to be stored are inserted. Access to the contents is had by peeling wall 111 away from wall 110, starting at the corner of the chevron. It is usually not necessary to completely remove the top wall to gain access, as illustrated in FIG. 11. As with the header type bag previously described, chevron type bags are well known and in common use. In the configurations of the prior art, however, they suffer from the same problems of having exposed unsterile areas in close proximity to the contained item while the item is being removed. This is avoided in the present invention by having a pair of fold out flaps 118 and 119 shield the contents of the bag from the unsterile area.

Flaps 118 and 119 are tack seamed to each other (120 and 121) and, when deployed, extend beyond the end of wall 110, as can be seen in FIG. 11. The flaps are made slightly narrower than the distance between seams 113 and 115 for some of their length so that they can be folded inside the package as shown in FIG. 12. At their other ends, flaps 118 and 119 are tack seamed to walls 110 and 111 respectively at seams 122 and 123. Flap 119 preferably has a cut out portion 124 so as to make grasping of the contents by the recipient easier. The size and shape of the cutout depends on the particular application, and in some cases it might be desirable to include a slit 126 in addition to or instead of cutout 124, so as to facilitate grasping of the bag contents. Alternatively, the contents of the pouch can be simply spilled out onto a sterile table without danger of contact with unsterile areas.

Figure 13:
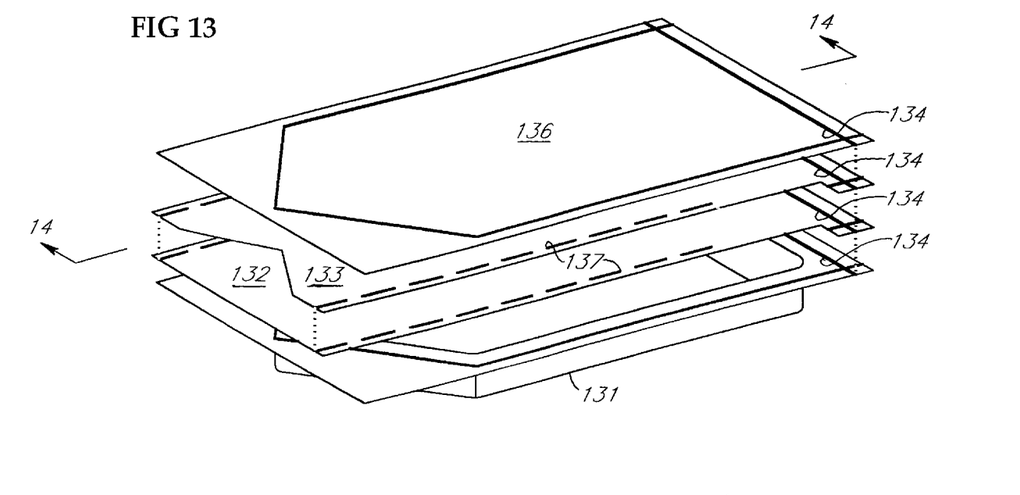
FIG. 13 is an exploded trimetric view of a fourth embodiment of the invented package. This embodiment uses a tray to hold the items to be stored.
Figure 14:
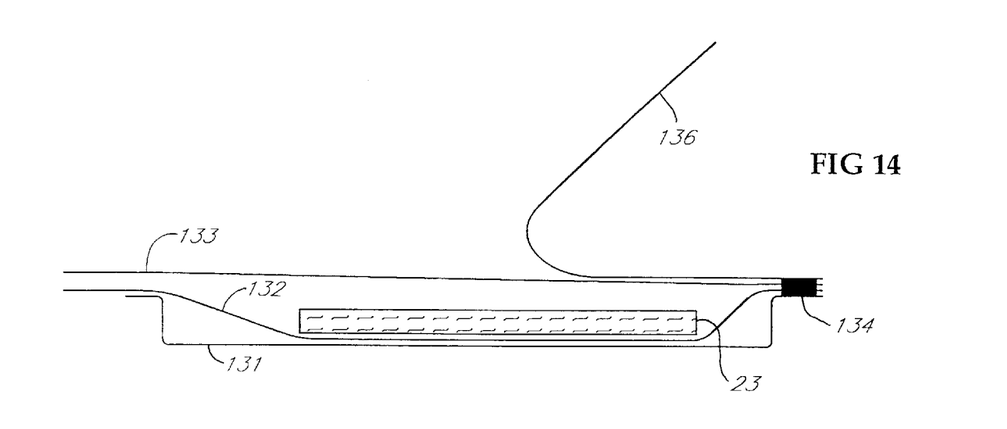
FIG. 14 is a cross sectional view of the package of FIG. 13, taken at 14—14 of FIG. 13. The package is shown open.
Figure 15:
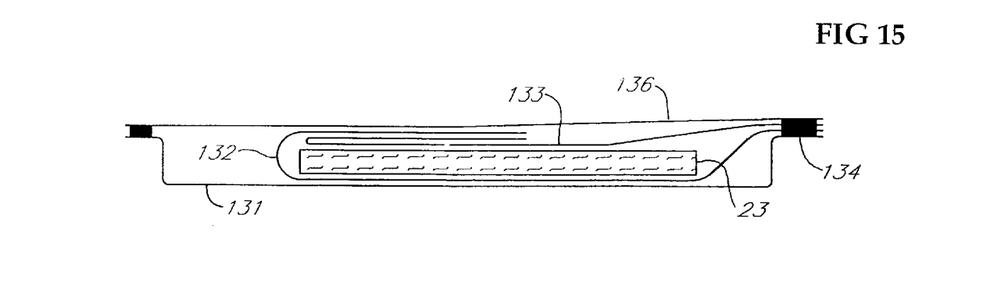
FIG. 15 is a cross sectional view of the fourth embodiment of the invention similar to FIG. 14 except that the package is shown closed.

FIGS. 13, 14, and 15 show the invention as applied to a chevron tray. In this embodiment, the contents are held in tray 131 between flaps 132 and 133, which are made narrow enough to fit inside the tray. Seam 134 anchors the flaps to the tray, and tack seams 135 and 137 create a chute to shield the contents when they are removed. As in the previous embodiment, and as illustrated in FIG. 14, top cover 136 is partially peeled off (from the chevron end) to remove the contents. Also, as in the previous embodiment, flaps 132 and 133 are folded inside before the seams around top cover 136 is made. This embodiment is different from the prior embodiments in that all of the seams around top cover 136 are made simultaneously.

Figure 16:
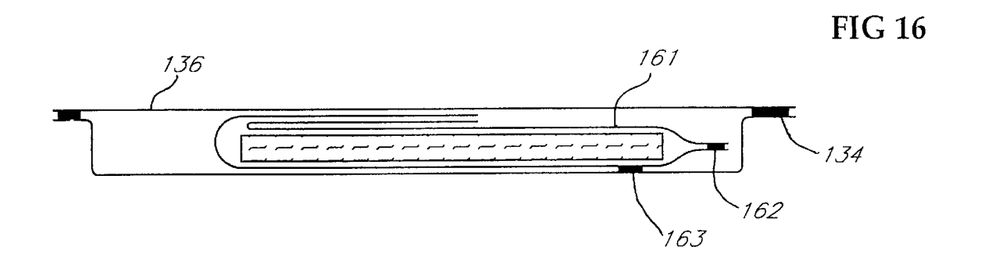
FIG. 16 is a cross sectional view of a variant of the embodiment of FIGS. 13–15. The figure is similar to FIG. 15.
Figure 17:
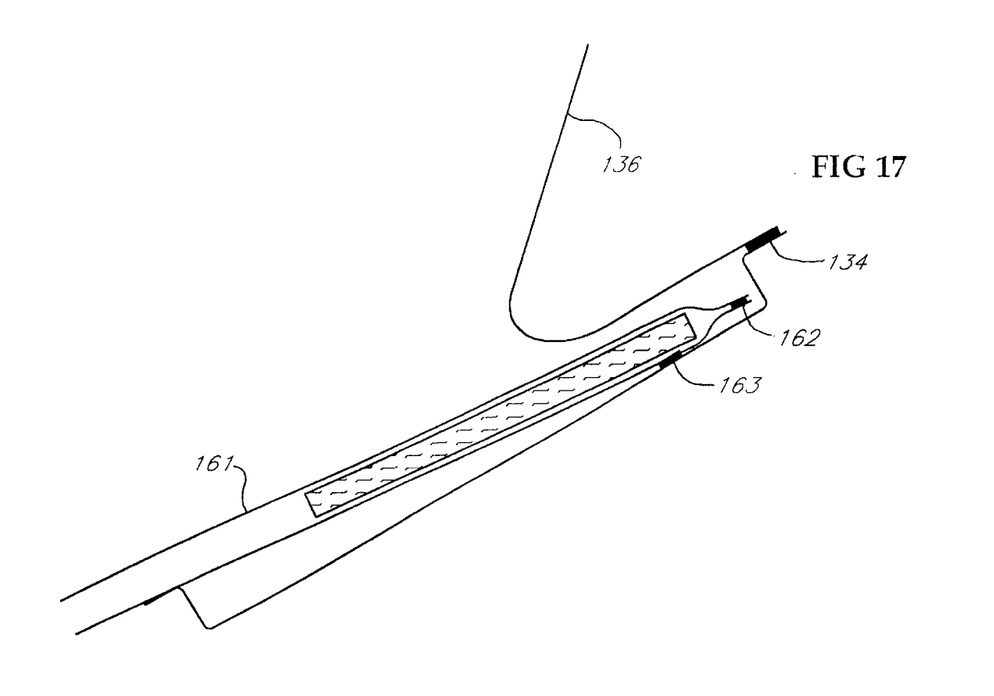
FIG. 17 is a cross sectional view of the package shown in FIG. 16, shown open.

FIGS. 16 and 17 depict a variant of the embodiment shown in FIGS. 13, 14, and 15 in that instead of the flaps being anchored to the tray by extending over the lip of the tray and being fastened by seam 134, the flaps take the form of a bag 161 which is closed on three sides (indicated by seam 162), and anchored, preferably by adhesive means, to the bottom of the tray (at 163). FIG. 17 shows how the container can be tilted to allow the contents, to slide out onto a table, if desired.

What has been invented is a novel packaging means for sterile items which preserves the integrity of the sterilization as the stored items are removed from the package. Several embodiments of the invention have been described in order that an understanding of the invention be conveyed. In particular, embodiments involving header and chevron type packages have been described in detail. However, the scope of the invention is not limited to these particular styles; as will be understood by those skilled in the art, the principles; disclosed are applicable to a wide variety of container constructions. Consequently, what is covered hereby should not be deemed limited to what has been described, but only by the scope of the appended claims.

We claim:

1. A sterilizable container for storing sterile items which comprises:
 a sterilizable storage volume comprised of first and second joined
  walls and having a peelably openable access opening;
 shielding means stored within said storage volume and deployable through said access opening for shielding said sterile items from unsterile areas of said container.

2. A sterilizable container as recited in claim 1 wherein said shielding means is comprised of a flap or a chute.

3. A sterilizable container as recited in claim 2 wherein said flap or chute is folded within said container and is deployed by unfolding.

4. A sterilizable container as recited in claim 1 wherein one of said joined walls is in the form of a tray.

5. A sterilizable container for containing sterile items which comprises:
 a first wall impervious to bacteria and the like;
 a second wall impervious to bacteria and the like;
 seams joining said first wall to said second wall and defining a closed storage volume between said walls, said storage volume having an interior and an exterior, at least a portion of said seams being peelable to define an access opening to said storage volume;
 a flap interior of said storage volume and deployable through said access opening.

6. A sterilizable container as recited in claim 5 wherein said first wall is comprised of a first part and a second part, said first part being seamed to said second wall, and said second part being a tear strip peelably seamed to said first part and to said second wall.

7. A sterilizable container as recited in claim 6 wherein said tear strip is permeable to sterilizing gases.

8. A sterilizable container as recited in claim 6 wherein said flap is attached to said first part along spaced lines, said sterile items being stored, at least partially, between said flap and said first part and between said spaced lines.

9. A sterilizable container as recited in claim 8 wherein said first part is folded on the interior of said storage volume and is deployable through said access opening.

10. A sterilizable container as recited in claim 5 wherein said flap forms part of a chute through which said items being stored are removed.

11. A sterilizable container as recited in claim 10 wherein said chute is folded within said storage volume.

12. A sterilizable container as recited in claim 5 wherein at least one side of said flap is colored a distinctive color different from the exterior of said storage volume.

13. A sterilizable container as recited in claim 5 and further including a tab attached to said flap.

14. A sterilizable container as recited in claim 5 and further including a chute comprised of a second flap attached to said flap along spaced lines, said second flap being attached to said first wall interior of said storage volume and said flap being attached to said first wall interior of said storage volume.

15. A sterilizable container as recited in claim 5 wherein said second wall is comprised of a tray.

16. A method for removing a sterile item from a container so as to preserve sterility which comprises the steps of:
 providing a container in which said sterile item has previously been inserted, sealed, and sterilized, said container having a peelably openable access opening and a deployable flap or chute internal to said sealed container; peeling open said access opening;
 deploying said flap or chute to form shield against any unsterile areas of said container in the path of removal of said sterile item;
 removing said sterile item from said container.

17. The method of removing a sterile item from a container as recited in claim 16 wherein said removing is accomplished by spilling said sterile item onto a sterile surface.

18. The method of removing a sterile item from a container as recited in claim 16 wherein said peeling open of said access opening is performed by a first person, and a second person removes said sterile item by grasping it and lifting it from said container.

* * * * *